(12) United States Patent
Nacouzi

(10) Patent No.: US 10,231,612 B2
(45) Date of Patent: Mar. 19, 2019

(54) LARYNGOSCOPE

(71) Applicant: Vincent Nacouzi, Raleigh, NC (US)

(72) Inventor: Vincent Nacouzi, Raleigh, NC (US)

( * ) Notice: Subject to any disclaimer, the term of this patent is extended or adjusted under 35 U.S.C. 154(b) by 682 days.

(21) Appl. No.: 14/418,734

(22) PCT Filed: Jul. 31, 2013

(86) PCT No.: PCT/US2013/053004
§ 371 (c)(1),
(2) Date: Jan. 30, 2015

(87) PCT Pub. No.: WO2014/022550
PCT Pub. Date: Feb. 6, 2014

(65) Prior Publication Data
US 2015/0173599 A1 Jun. 25, 2015

Related U.S. Application Data

(60) Provisional application No. 61/790,913, filed on Mar. 15, 2013, provisional application No. 61/677,922, filed on Jul. 31, 2012.

(51) Int. Cl.
A61B 1/267 (2006.01)
A61B 1/07 (2006.01)
(Continued)

(52) U.S. Cl.
CPC ............ A61B 1/267 (2013.01); A61B 1/07 (2013.01); A61B 13/00 (2013.01); A61M 16/0488 (2013.01)

(58) Field of Classification Search
CPC ........... A61B 13/00; A61B 1/07; A61B 1/267; A61B 1/00064; A61B 1/0055–1/0056; A61B 1/32; A61B 1/025; A61M 16/0488
(Continued)

(56) References Cited

U.S. PATENT DOCUMENTS 1,568,732 A * 1/1926 Haslinger .......... A61B 1/00098
600/196
2,858,826 A * 11/1958 Kahn .................. A61B 1/32
600/221
(Continued)

FOREIGN PATENT DOCUMENTS

DE 29921801 U1 3/2000
WO 9730626 A1 8/1997

OTHER PUBLICATIONS

Nacouzi, Vincent, International Application No. PCT/US2013/053004, International Preliminary Report on Patentability, dated Feb. 3, 2015.
(Continued)

Primary Examiner — Zade Coley
Assistant Examiner — Jessica Weiss
(74) Attorney, Agent, or Firm — Taylor English Duma LLP

(57) ABSTRACT

A laryngoscope is described for inserting into a mouth of a patient having a tongue, the laryngoscope comprising a handle and an elongate blade detachably fixed to the handle in a plane angularly disposed with respect to the longitudinal axis of the handle. The blade includes a stationary portion and a movable portion having a surface for engaging the tongue of the patient, the movable portion mounted to the stationary portion of the blade for rotation about an axis substantially along the longitudinal axis of the blade. An operating member is manipulated by user for rotating the movable portion of the blade, wherein laryngoscopy of the patient by manipulation of the handle includes at least a rotating motion of the movable portion of the blade.

4 Claims, 20 Drawing Sheets

(51) Int. Cl.
*A61B 13/00* (2006.01)
*A61M 16/04* (2006.01)

(58) Field of Classification Search
USPC ................. 600/185–200, 220, 235, 244
See application file for complete search history.

(56) References Cited

U.S. PATENT DOCUMENTS

| | | | | |
|---|---|---|---|---|
| 3,363,622 | A * | 1/1968 | Mendola | A61B 13/00 433/140 |
| 4,295,465 | A * | 10/1981 | Racz | A61B 1/267 600/190 |
| 5,498,231 | A * | 3/1996 | Franicevic | A61B 1/267 128/200.26 |
| 5,584,795 | A * | 12/1996 | Valenti | A61B 1/042 600/196 |
| 5,776,053 | A * | 7/1998 | Dragisic | A61B 1/267 600/195 |
| 5,954,632 | A * | 9/1999 | Heckele | A61B 1/32 600/104 |
| 6,095,972 | A * | 8/2000 | Sakamoto | A61B 1/267 600/190 |
| 6,960,166 | B1 * | 11/2005 | Wong | A61B 8/12 600/221 |
| 6,991,604 | B2 * | 1/2006 | Cantrell | A61B 1/00094 600/185 |
| 7,153,260 | B1 * | 12/2006 | Girgis | A61B 1/267 600/193 |
| 7,371,212 | B2 * | 5/2008 | Klaassen | A61B 1/32 600/220 |
| 9,011,322 | B2 * | 4/2015 | Estrada | A61B 1/267 600/194 |
| 2005/0054903 | A1 * | 3/2005 | Cantrell | A61B 1/00094 600/196 |
| 2010/0261968 | A1 | 10/2010 | Nearman et al. | |
| 2012/0083658 | A1 * | 4/2012 | Hahn | A61B 1/32 600/205 |

OTHER PUBLICATIONS

Nacouzi, Vincent, International Application No. PCT/US2013/053004, International Search Report, dated Nov. 8, 2013.

* cited by examiner

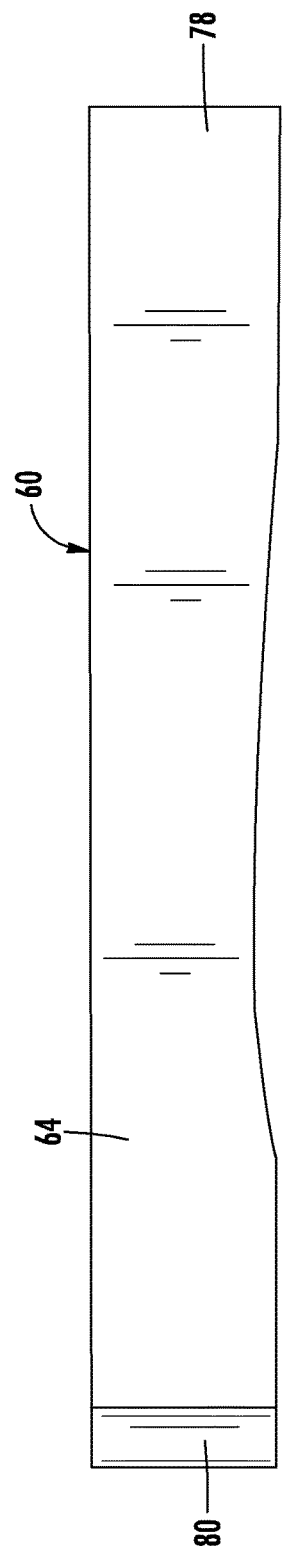
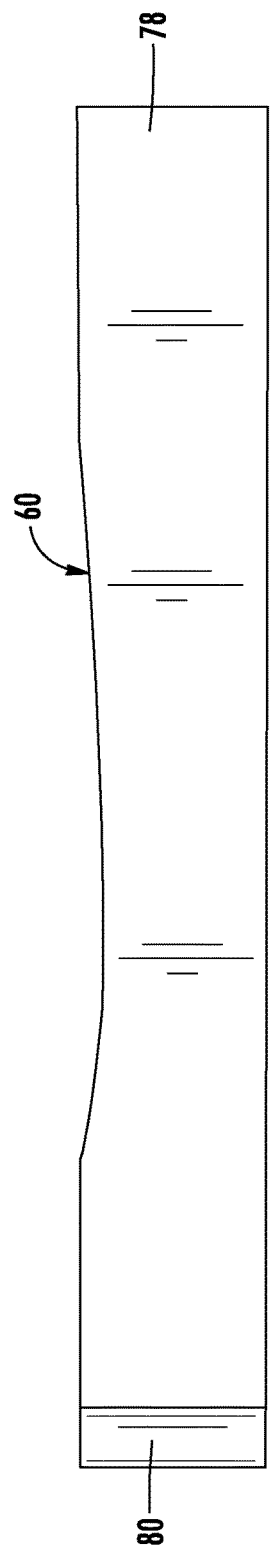

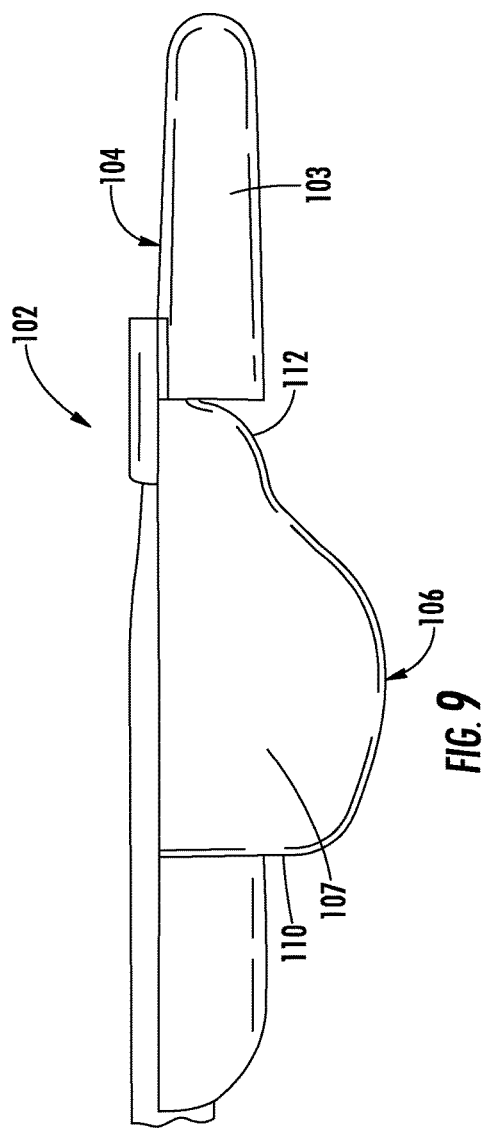
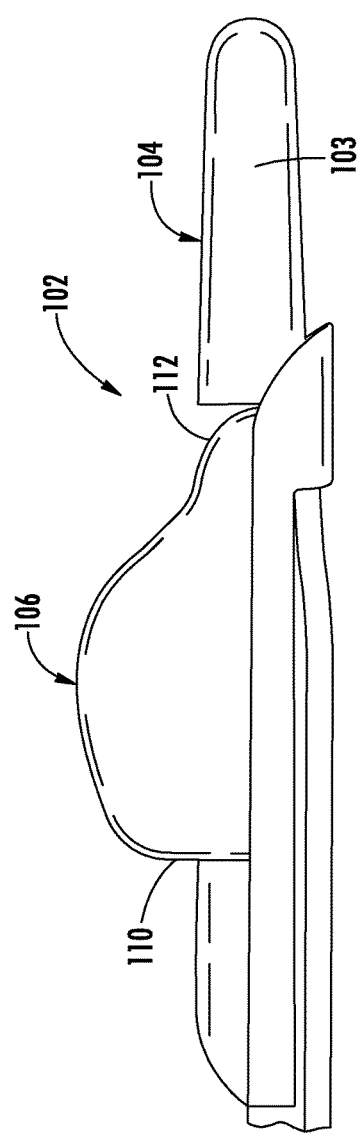

LARYNGOSCOPE

CROSS-REFERENCES

This application is related to U.S. provisional application No. 61/677,922, filed Jul. 31, 2012, entitled "Laryngoscope", and naming Vincent Nacouzi as the inventor, and U.S. provisional application No. 61/790,913, filed Mar. 15, 2013, entitled "Laryngoscope", and naming Vincent Nacouzi as the inventor. The contents of both provisional applications are incorporated herein by reference in their entirety, and the benefit of the filing dates of the provisional applications are hereby claimed for all purposes that are legally served by such claim for the benefit of the filing dates.

BACKGROUND

A laryngoscope is described and shown for use in opening an airway for orotracheal intubation and, more particularly, a laryngoscope for simultaneously displacing the tongue muscle and associated tissue for exposing the larynx and the glottis for intubating a patient with an endotracheal tube.

Oral or nasal endotracheal intubation procedures are commonly employed to secure a controlled airway and to deliver inhalant oxygen, anesthetic gases, and other therapeutic agents into the trachea and lungs of human and veterinary patients. Laryngeal exposure to visualize vocal cords and facilitate airway control through intubation is a key element in anesthesia and emergency medicine rapid sequence intubation. A laryngoscope is a key instrument for intubation procedures.

A conventional laryngoscope typically includes a handle and a blade. A proximal end of the blade is detachably connected to an end of the handle such that the blade extends generally normally forwardly from the handle in an L-shaped configuration. Many types of laryngoscope blades have been developed, each characterized by blade curvature, the point of such curvature, and the flange structure of the blade. The primary function of the laryngoscope in orotracheal intubation is to open the mouth and expose the larynx in order to facilitate the insertion of the endotracheal tube into the trachea. The laryngoscope blade serves to displace the tongue and allow direct visualization of the vocal cords through the mouth opening.

During intubation, a patient is often paralyzed with paralytic drugs or unconscious and not spontaneously breathing. With seconds or minutes to secure an airway, the patient is placed in a supine position with the head tilted backwardly. The laryngoscope blade is usually inserted laterally from the right side of the mouth in order to sweep the tongue mass to the left. The blade is then directed medially to engage and deflect the tongue away from the lumen of the pharyngeal outlet for adequate visualization of the vocal cords. The laryngoscope may be further manipulated to expose the glottic opening. The endotracheal tube is then introduced through the mouth and visually advanced, passing between the vocal cords into the subglottic space for securing the airway. Once placement of the endotracheal tube has been achieved, the laryngoscope blade is removed.

Intubation procedures involving laryngoscopy require training, skill and strength. Much of the effort goes to moving the large mass of the tongue to expose the airway and visualize the vocal cords. Unfortunately, only a small portion of the surface of the conventional blade can be used efficiently to move the tongue. Moreover, during insertion of the laryngoscope, care must be taken to avoid pressure on the teeth and gums of the patient and avoid traumatizing both the oral mucosa and the epiglottis. The process of laryngoscopy requires a levering action with a fulcrum around the upper teeth. This much needed important levering action is limited by the size of the mouth opening and is insufficient for sweeping aside the tongue mass, particularly in view of the distance of the tongue mass from the mouth opening. Because the laryngoscope blade is necessarily formed of a hard, inflexible material, and the manipulation awkward and challenging, dental damage is a potential result when significant pressure is exerted, which all too often is a risk when performing laryngoscopy. This is certainly accentuated in patients with difficult and narrow airways, due their neck length, body habitus, pharyngeal space opening, tongue size and other pertinent variances.

For the foregoing reasons, and with challenging small and difficult airways, there is a need for a new laryngoscope blade for simultaneously opening the mouth and deflecting the tongue muscle away from the opening of the trachea for exposing and visualizing the larynx and the vocal cords.

SUMMARY

A laryngoscope is described for inserting into a mouth of a patient having a tongue, the laryngoscope comprising a handle and an elongate blade detachably fixed to the handle in a plane angularly disposed with respect to the longitudinal axis of the handle. The blade includes a stationary portion and a movable portion having a surface for engaging the tongue of the patient, the movable portion mounted to the stationary portion of the blade for rotation about an axis substantially along the longitudinal axis of the blade. An operating member is manipulated by user for rotating the movable portion of the blade, wherein laryngoscopy of the patient by manipulation of the handle includes at least a rotating motion of the movable portion of the blade.

In another aspect, a laryngoscope is described for inserting into a mouth of a patient having a tongue, the laryngoscope comprising a handle and an elongate blade detachably fixed to the handle in a plane angularly disposed with respect to the longitudinal axis of the handle. The blade includes a stationary portion and a pivoting portion pivotally secured to the stationary portion of the blade at a pivot point. A movable portion of the blade having a surface for engaging the tongue of the patient is mounted to the pivoting portion of the blade for rotation about an axis substantially along the longitudinal axis of the blade. An operating member is manipulated by user for rotating the movable portion of the blade, wherein laryngoscopy of the patient by manipulation of the handle includes at least a pivoting motion and a rotating motion of the portions of the blade.

BRIEF DESCRIPTION OF THE DRAWINGS

For a more complete understanding of the laryngoscope, reference should now be had to the embodiments shown in the accompanying drawings and described below. In the drawings:

FIG. 4 is a top plan view of a blade for use with the laryngoscope as shown in FIG. 1

FIG. 5 is a bottom plan view of the blade as shown in FIG. 4.

FIG. 9 is a top plan view of a blade for use with the laryngoscope as shown in FIG. 8.

FIG. 10 is a bottom plan view of the blade as shown in FIG. 9.

DESCRIPTION

Certain terminology is used herein for convenience only and is not to be taken as a limitation on the invention. For example, words such as "upper," "lower," "left," "right," "horizontal," "vertical," "upward," and "downward" merely describe the configuration shown in the FIGS. Indeed, the components may be oriented in any direction and the terminology, therefore, should be understood as encompassing such variations unless specified otherwise.

Figure 1:
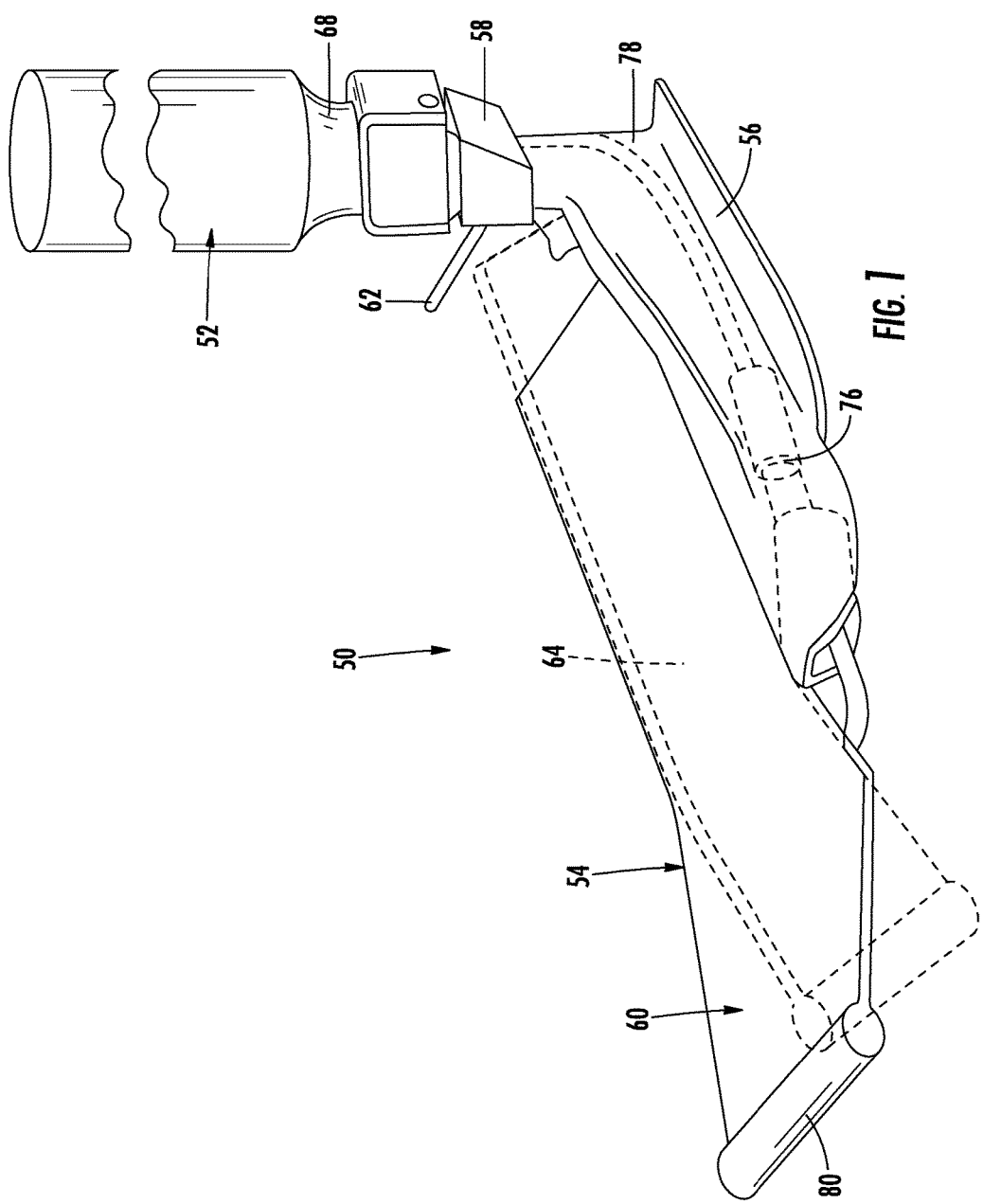
FIG. 1 is a front left perspective view of a laryngoscope with a portion of a blade shown in a first position and a second position depicted in dashed lines.
Figure 2:
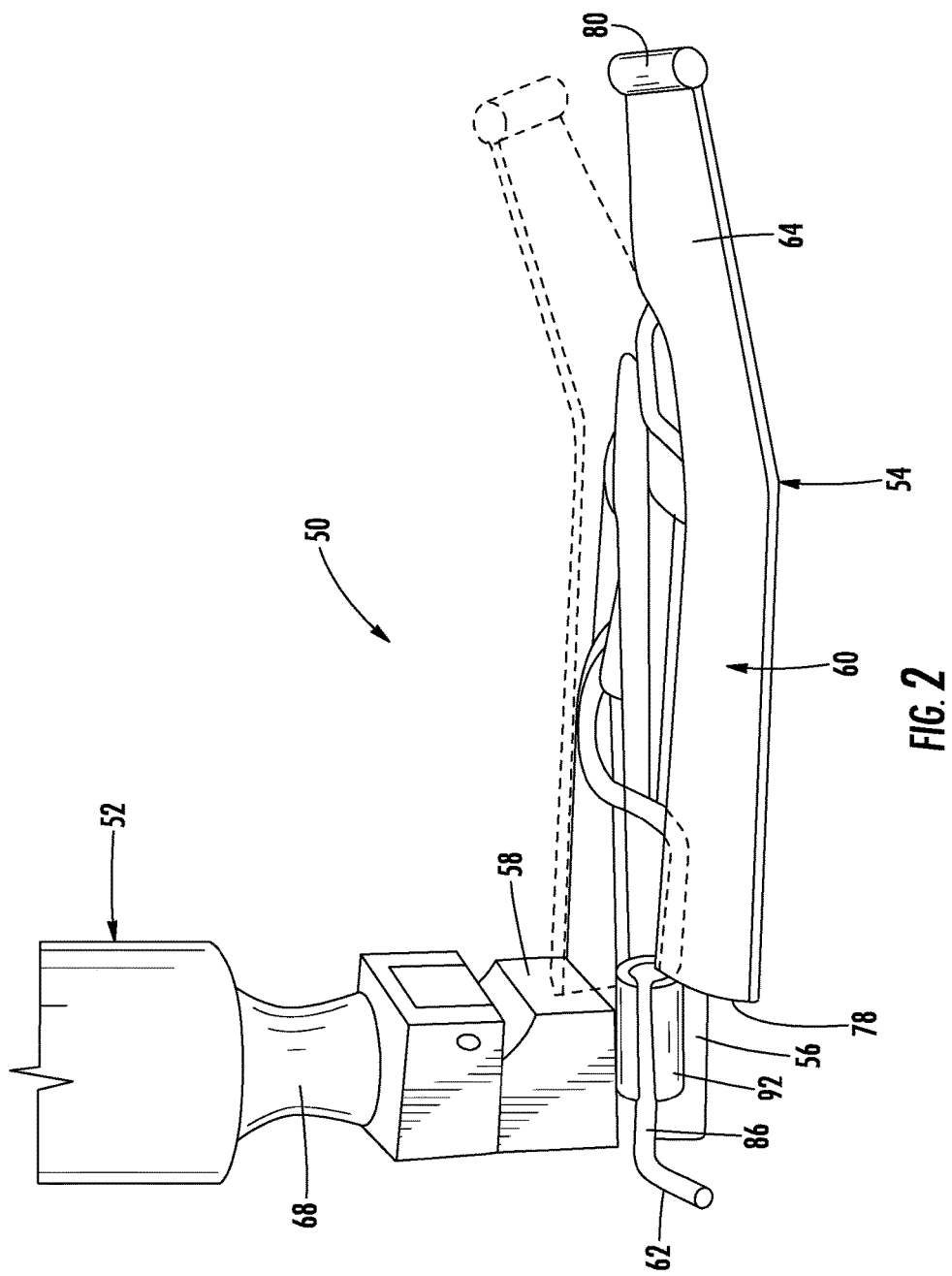
FIG. 2 is a right side elevation view of the laryngoscope as shown in FIG. 1 with the portion of the blade shown in the first position and the second position depicted in dashed lines.
Figure 3:
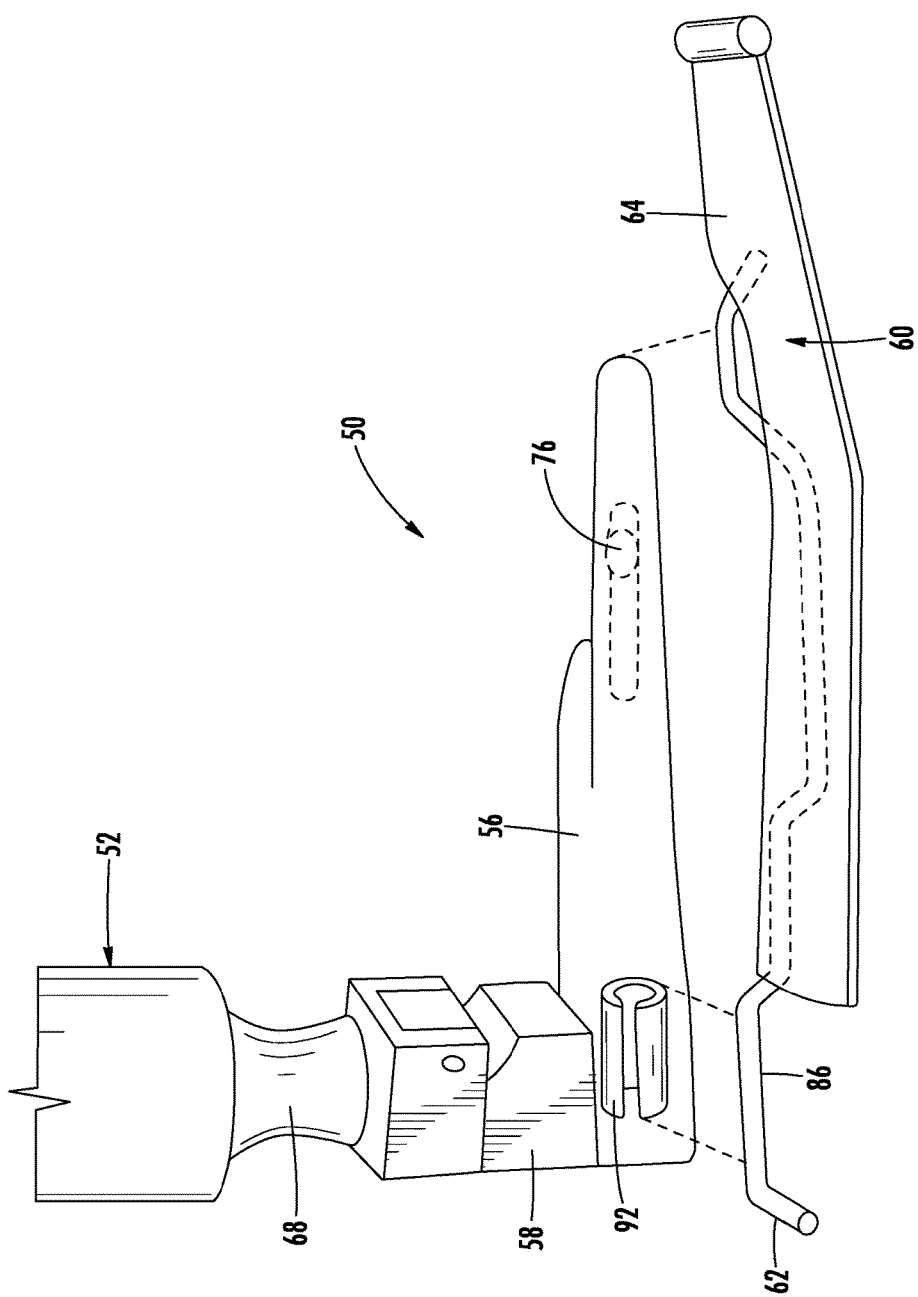
FIG. 3 is an exploded perspective view of the laryngoscope as shown in FIG. 1.

Referring now to the drawings, wherein like reference numerals designate corresponding or similar elements throughout the several views, an embodiment of a laryngoscope is shown in FIGS. 1-3 and generally designated at 50. The laryngoscope 50 comprises a cylindrical handle 52 and a blade 54, the blade 54 including a stationary portion 56 and a tongue deflector 60. The tongue deflector 60 is rotatable about the longitudinal axis of the blade 54 relative to the stationary portion 56 of the blade 54. As will be described herein, the tongue deflector 60 may be rotated to an angular position with respect to the stationary portion 56 of the blade 54 by means of an operating lever 62 manipulated by the user. The tongue deflector 60 may optionally be locked in the angular position.

The handle 52 has a proximal end 66 and a distal end 68. In one embodiment, the handle 52 is a conventional laryngoscope handle. In certain aspects, the handle 52 may include a power source, such as a battery, as well as other interfaces of mechanical or electrical means known to one of ordinary skill in the art.

The blade 54 has a proximal end 78 and a distal end 80. The blade 54 is formed from a substantially rigid material to allow adequate physical retraction of anatomic structures during use of the laryngoscope. Accordingly, the blade 54 may be constructed of metal or metal alloys that are capable of repeated use and for withstanding sterilization between uses. Suitable metal or metal alloys include stainless steel or aluminum. Alternatively, the blade 54 may be constructed of any rigid plastic that is suitable for medical use, or other low cost, sterile material, and may be provided as a single-use, disposable unit. It is understood that the blade 54 may also be made wholly, or in part, of any other suitable rigid material known in the art. Moreover, it is understood that the scope of the invention is not intended to be limited by the materials listed here, but may be carried out using any material which allows the construction and operation of the laryngoscope described herein.

The proximal end 78 of the blade 54 may be connected to the distal end 68 of the handle 52 in a known manner. In one embodiment, a conventional mechanical interface 58 is provided at the proximal end 78 of the stationary portion of the blade 54 for connection to the handle 52. More particularly, the mechanical interface 58 comprises an engagement hook, which is sized and positioned to engage a transverse pivot pin of a conventional laryngoscope handle 52. The mechanical interface 58 is configured to allow the blade 54 to functionally mount to the distal end 68 of the handle 52 for movement with the handle. In one embodiment, the joined handle 52 and blade 54 define an angle of about 90 degrees and can vary up to 110 degrees in some configurations. More particularly, the longitudinal axis of the handle 52 is perpendicular to a plane normal to the tongue-contacting surface 64 of the tongue deflector 60. In another embodiment, the proximal end 78 of the blade 54 may be attached to the distal end 68 of the handle 52 by screw thread engagement means (not shown). Alternatively, the handle 52 and the blade 54 may be integrally formed together.

In another aspect, the blade 54 may provide for other mechanical, as well as electrical, interfaces with the handle 52. In this arrangement, the blade 54 interlocks with the handle 52 in such a way as to make mechanical and electrical communication with the handle. For example, wiring may be provided from the handle 52 to a miniaturized lamp 76 for illumination at or toward the distal end 80 of the blade 54 during use. Alternatively, fiber optic illumination may be employed using fiber optic carriers within the blade 54 that may be supplied by either an external light source or by a conventional light source contained within the handle 52, or by an internal lamp 76 housed proximally within the blade 54. The stationary blade portion 56 may also carry, or be adapted to provide, lighting means such as are known in the art for directing light at the distal end 80 of the blade 54.

The tongue deflector 60 is an elongated substantially rectangular member (FIGS. 4 and 5) and may be slightly curved upwardly toward the handle 52 at the distal end 80 of the blade 54. Although the tongue deflector 60 is shown as slightly curved, it is understood that the blade may also be provided in a substantially straight configuration. The tongue deflector 60 is rotatably mounted to the stationary portion 56 of the blade 54 so that the tongue deflector 60 can rotate relative to the stationary portion 56. As best seen in FIG. 3, a rigid rod 86 is provided for actuating the rotation of the tongue deflector 60. A portion of the rod 86 is fastened longitudinally along the lower surface of the tongue deflector 60. At least the proximal end 88 of the rod 86 is journaled in a tubular sleeve 92 fixed to the surface of the stationary blade portion 56. This arrangement allows the tongue deflector 60 and the rod 86 to pivot freely about a rotational axis coincident with the longitudinal axis of the blade 54. The tongue deflector 60 can thus articulate, which means movement upward, downward, or in a circular or elliptical path along or about the axis of rotation. It is understood that, in one embodiment, the rod 86 can be spring-biased (not shown) to return the tongue deflector 60 to the home position. It is further understood that the tongue deflector 60 may be pivotally mounted to the blade 54 by any conventional means, such as ball and socket joints, hinges, straps, and the like.

Figure 6:
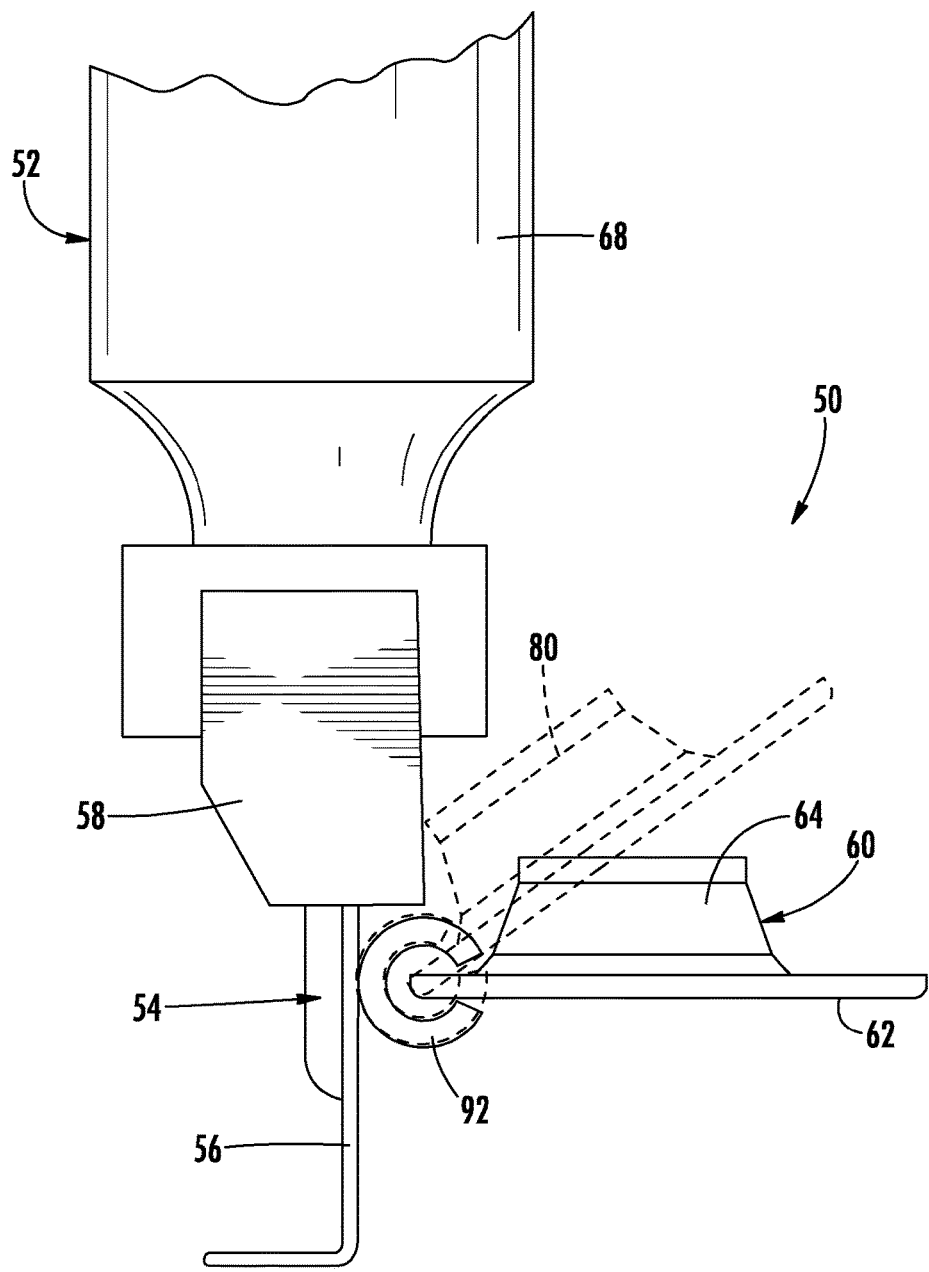
FIG. 6 is a rear elevation view of the laryngoscope as shown in FIG. 1 with the portion of the blade shown in the first position and the second position depicted in dashed lines.
Figure 7:
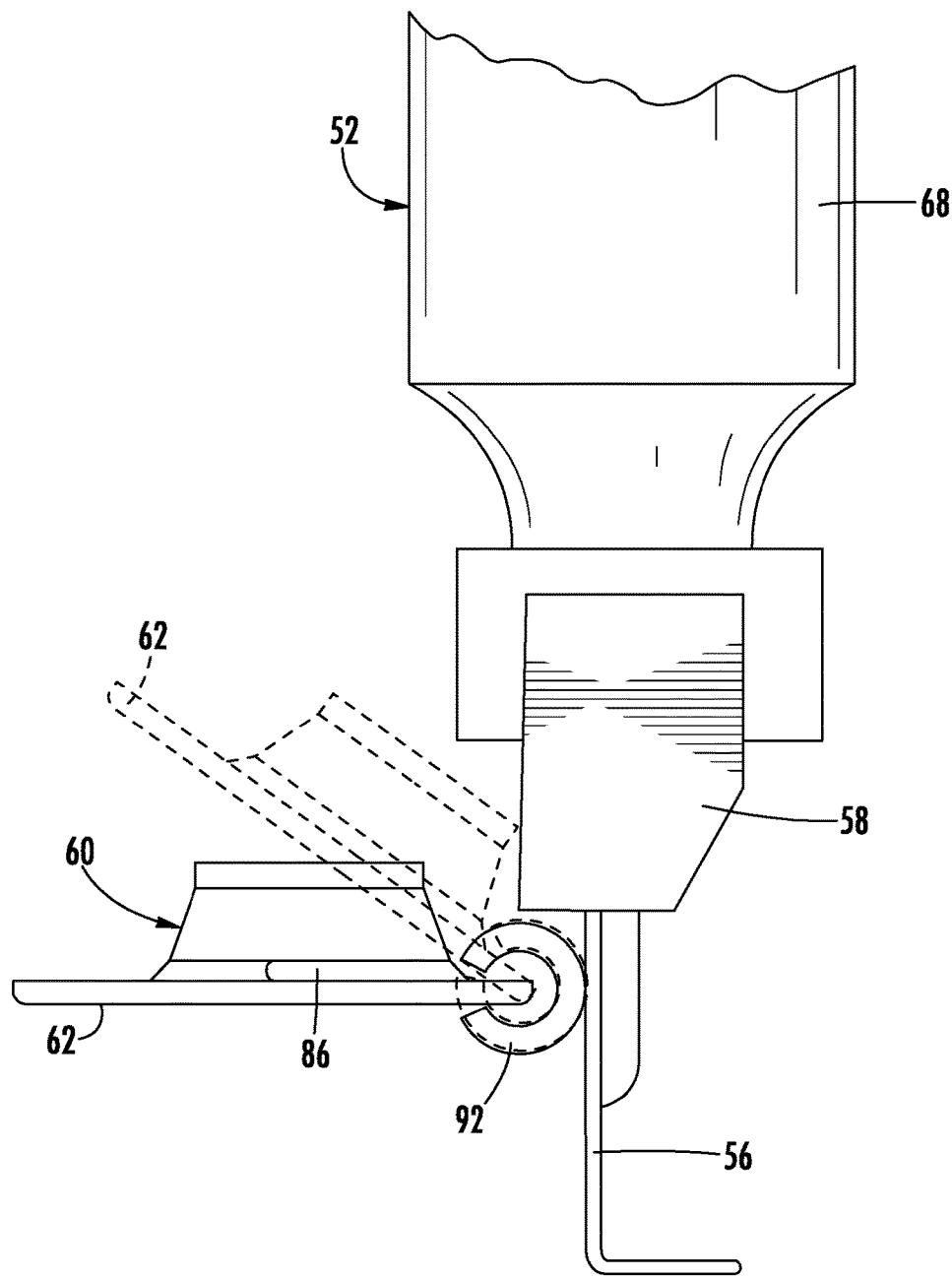
FIG. 7 is a front elevation view of the laryngoscope as shown in FIG. 1 with the portion of the blade shown in the first position and the second position depicted in dashed lines.
Figure 8:
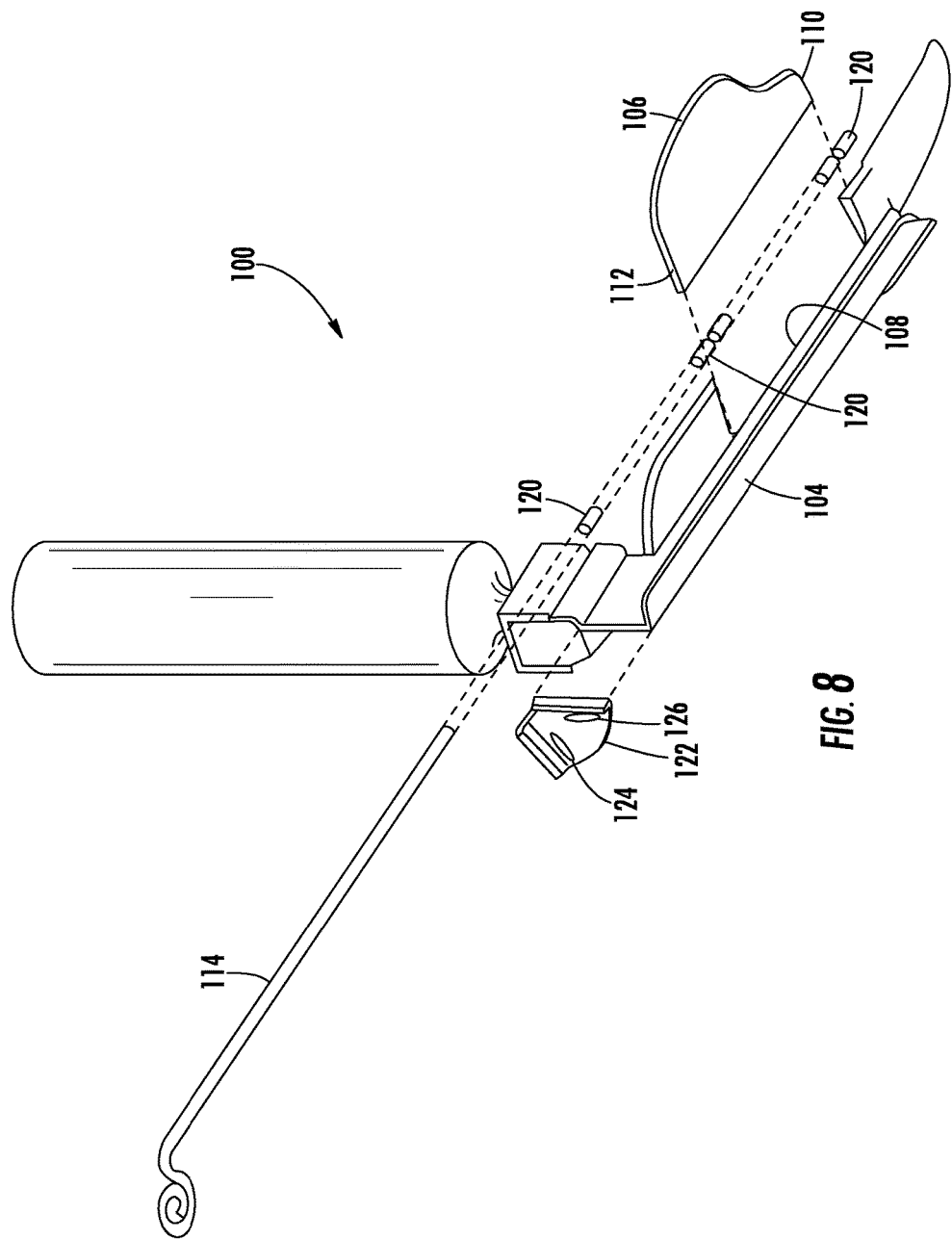
FIG. 8 is an exploded perspective view of a second embodiment of a laryngoscope.

Means are provided for actuating the rotational movement of the tongue deflector 60. In the embodiment of the laryngoscope 50 shown in FIGS. 1-7, the proximal end 88 of the rod 86 is turned outwardly proximally of the sleeve 92 forming the lever 62. Referring to FIGS. 6 and 7, the tongue deflector 60 is pivoted by manually rotating the lever 62 relative to the blade 54, which simultaneously rotates the rod 86 within the sleeve 92. Accordingly, a pivoting force can be easily transmitted to the tongue deflector 60 using the lever 62 by the action of the fingers in turning the wrist. Alternatively, the lever 62 can be connected to actuation means (not shown) mechanically or electrically, such as by a programmable logic controller (PLC) or controller with logic to determine which functions to execute to actuate the tongue deflector 60. The actuation mechanism can be a motor in the handle 52 responsive to an electronic stimulus or a signal.

In use, rotation of the tongue deflector 60 relative to the stationary portion 56 of the blade 54 causes the tongue-contacting surface 64 of the tongue deflector 60 to move the tongue and associated tissue to expose the vocal cords and the glottis of a patient. The user is typically working from a position above the head of a supine patient. The head of the patient is stabilized and the mouth is opened. For a right-handed user, the handle 52 of the laryngoscope 50 is usually held in the left hand, with the blade 54 oriented downwardly away from the user. The blade 54 is inserted into the mouth of the patient until the distal end of the blade 54 is positioned at the junction between the base of the tongue and the base of the epiglottis.

With one hand holding the handle 52 of the laryngoscope 50, the user rotates the-lever 62 using the thumb or fingers of the other hand for rotation of the tongue deflector 60. When the lever 62 is rotated relative to the blade 54, the rod 86 and connected tongue deflector 60 are rotated about their rotation axis, causing the tongue deflector 60 to assume an angular position with respect to the stationary portion of the blade 54. This action sweeps the tongue and exposes the larynx. The tongue deflector 60 functions to hold back tissue that would otherwise obscure the vision of the user and block the airway as well as maintaining airway patency. The user may then intubate the patient. The larynx is visualized off the medial side of the laryngoscope blade 54 where the endotracheal tube or other instruments can be introduced.

A second embodiment of a laryngoscope is shown in FIGS. 8-12 and generally designated at 100. The laryngoscope 100 comprises a blade 102, including a stationary portion 104 and a tongue deflector 106. The upper major surface of the stationary portion 104 of the blade 102 is a tongue-contacting surface 103. The stationary portion 104 of the blade 102 defines a transverse recess 108 intermediate along the length of the blade for receiving the tongue deflector 106.

The tongue deflector 106 has a proximal end 110 and a distal end 112. The tongue deflector 106 is configured to be received, at least partially, in the recess 108 in the stationary portion 104 of the blade 102. In this configuration, the tongue deflector 106 extends substantially along the length of the blade 102. The tongue deflector 106 is mounted for rotation about the longitudinal axis of the stationary portion 104 of the blade 102. In a first, home position of the tongue deflector 106, the edges of the tongue deflector 106 are abutted flush with the corresponding edges of the stationary portion 104 of the blade 102 defining the recess 108. The tongue deflector 106 is configured so that a tongue-contacting surface 107 of the tongue deflector 106 is substantially flush with the upper tongue contacting surface 103 of the stationary portion 104 of the blade 102. The surface of the tongue deflector 106 is shaped so as to provide surface continuity of the blade 102 when the tongue deflector 106 is in the home position. In this arrangement, the tongue deflector 106 provides no greater bulk that might obstruct either the visual field or working access distal to the tongue deflector 106 during an intubation procedure.

The tongue deflector 106 extends wider than the blade 102 and is generally planar along its length. Referring to FIGS. 9 and 10, the proximal end 110 of the tongue deflector 106 is wider than the blade 102 and tapers in a curvilinear manner to the distal end 112 of the tongue deflector 106 where the tongue deflector is the same width as the stationary portion 104 of the blade 102. Although the outer edge of the blade 102 is shown as slightly curved, it is understood that the blade 102 may also be provided in a substantially rectangular configuration or any other suitable shape.

As with the previous embodiment of the laryngoscope, the tongue deflector 106 may be rotated to an angular position with respect to the stationary portion 104 of the blade 102 by means of an operating lever 62 manipulated by the user. In this embodiment, an elongate rod 114 is provided having at least a proximal end 116 and a distal end 118 journaled in tubular sleeves 120 fixed to the surface of the blade 102. This arrangement allows the tongue deflector 106 and the rod 114 to pivot freely about a rotational axis.

Figure 11:
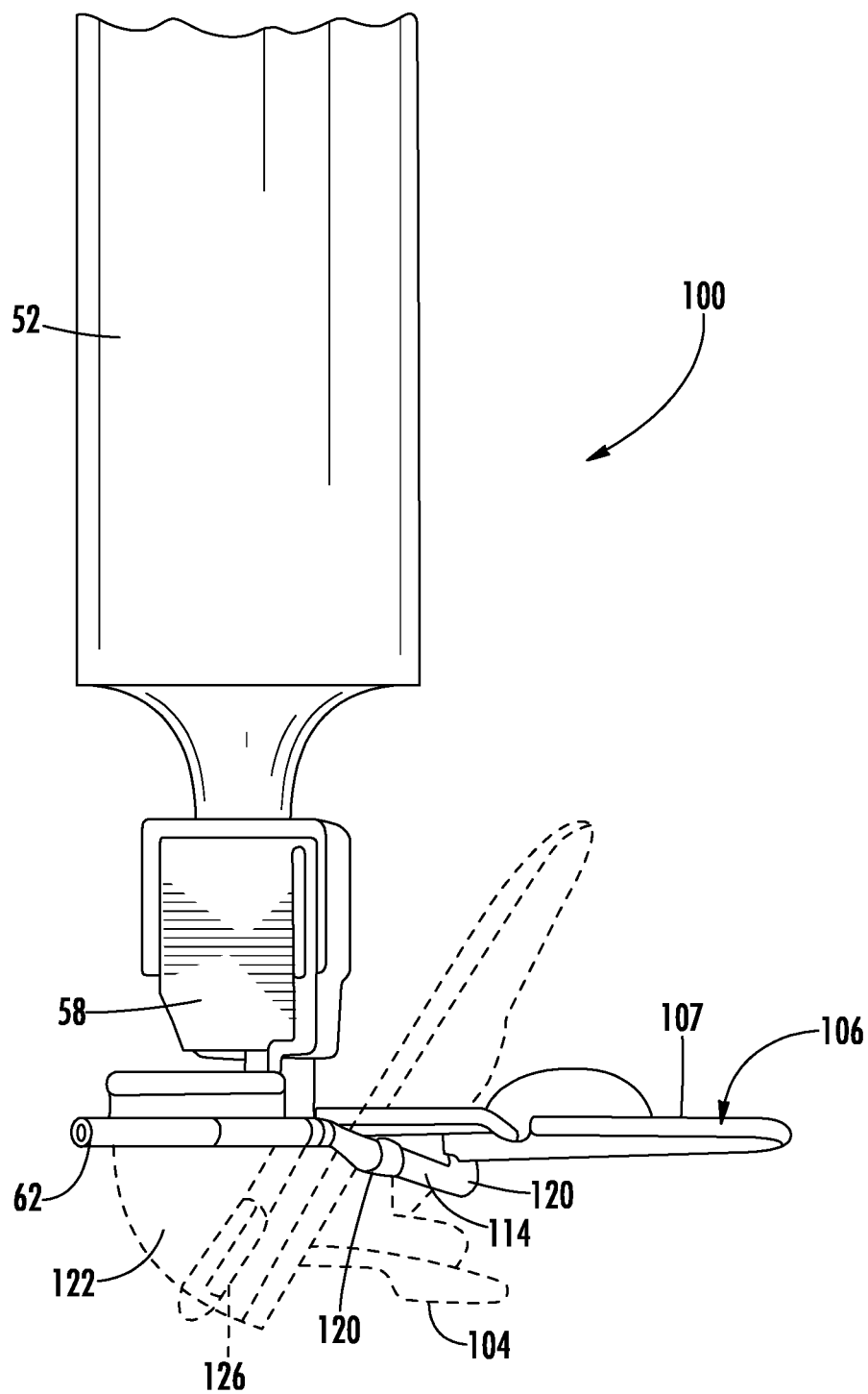
FIG. 11 is a rear elevation view of the laryngoscope as shown in FIG. 8 with a portion of the blade shown in a first position and a second position depicted in dashed lines.

Referring to FIG. 11, the tongue deflector 106 may optionally be locked in the angular position. In this embodiment, the lever comprises a curled free end of the rod 114. An end wall 122 of the blade 102 defines an opening for passing the rod 114 and is adapted to fixedly receive the lever 62 so as to maintain the relative position of the tongue deflector 106 in use. More particularly, the end wall 122 comprises a locking mechanism having a first opening 124 and a second opening 126 adjacent to, and along the path of rotation of the lever 62. The first opening 124 corresponds to the home position of the tongue deflector 106. The second opening 126 corresponds to the angular position of the tongue deflector 106 relative to the stationary portion 104 of the blade 102. The locking mechanism maintains the tongue deflector 106 in a desired angular position relative to the blade 102 by locking the lever 62 and integral rod 114. The tongue deflector 106 thus remains in position without requiring the hands of the user. Removing the lever 62 from the second opening 126 releases the lever 62 and allows the tongue deflector 106 to return to the original home position flush with the surfaces of the blade 102.

Figure 12:
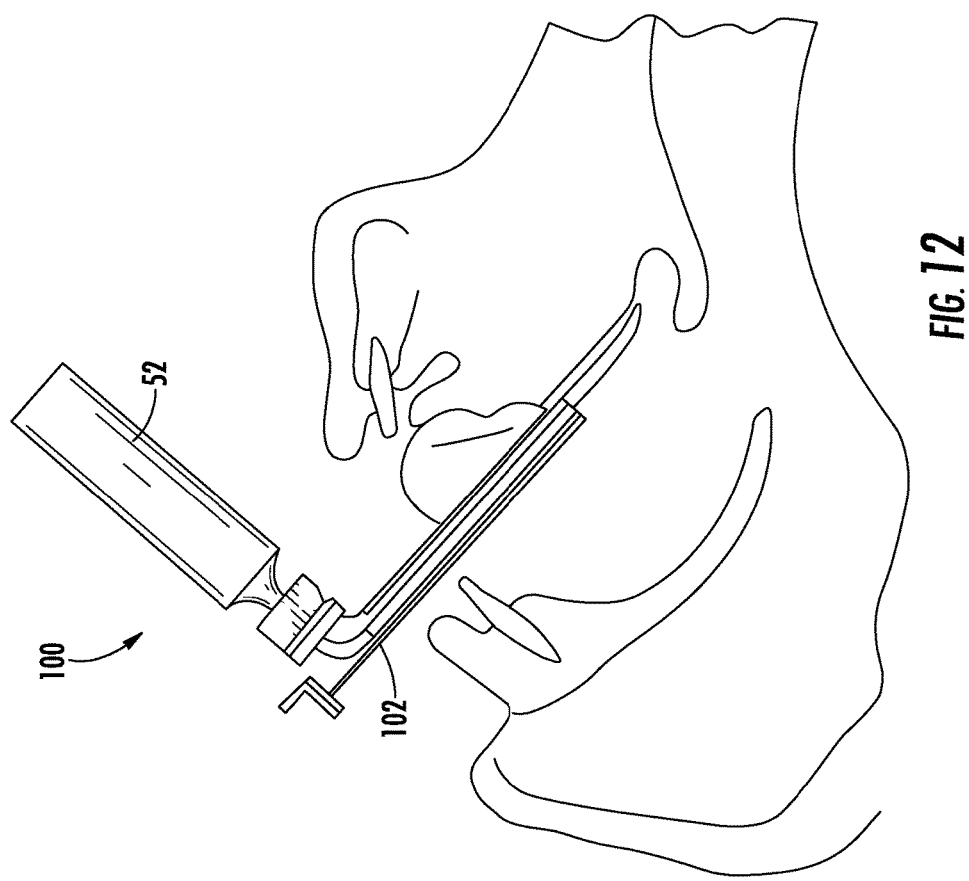
FIG. 12 is schematic cross-section view of the laryngoscope as shown in FIG. 8 in position for use in a mouth of a patient.
Figure 13:
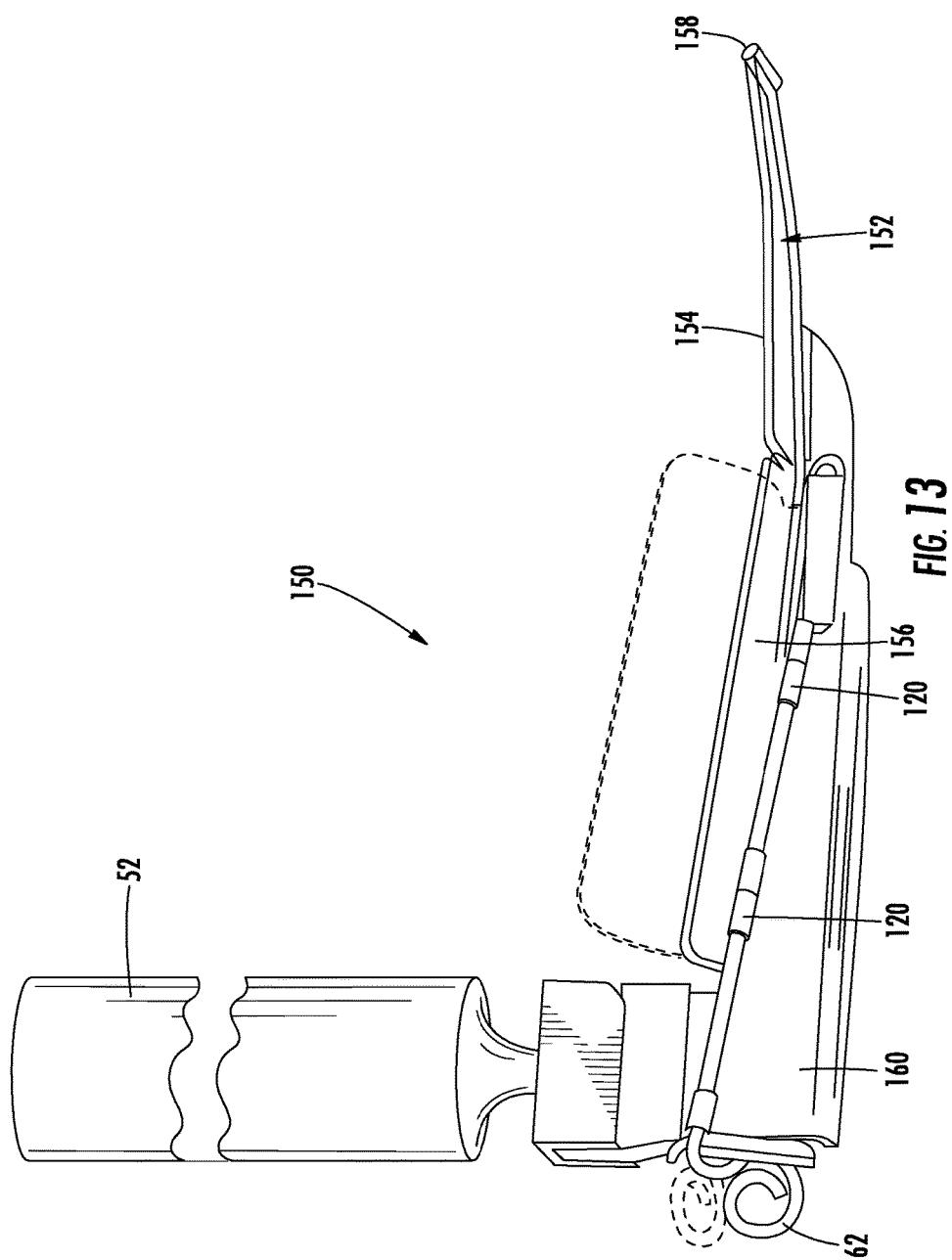
FIG. 13 is a right side elevation view of a third embodiment of a laryngoscope with a portion of a blade shown in a first position and a second position depicted in dashed lines.
Figure 14:
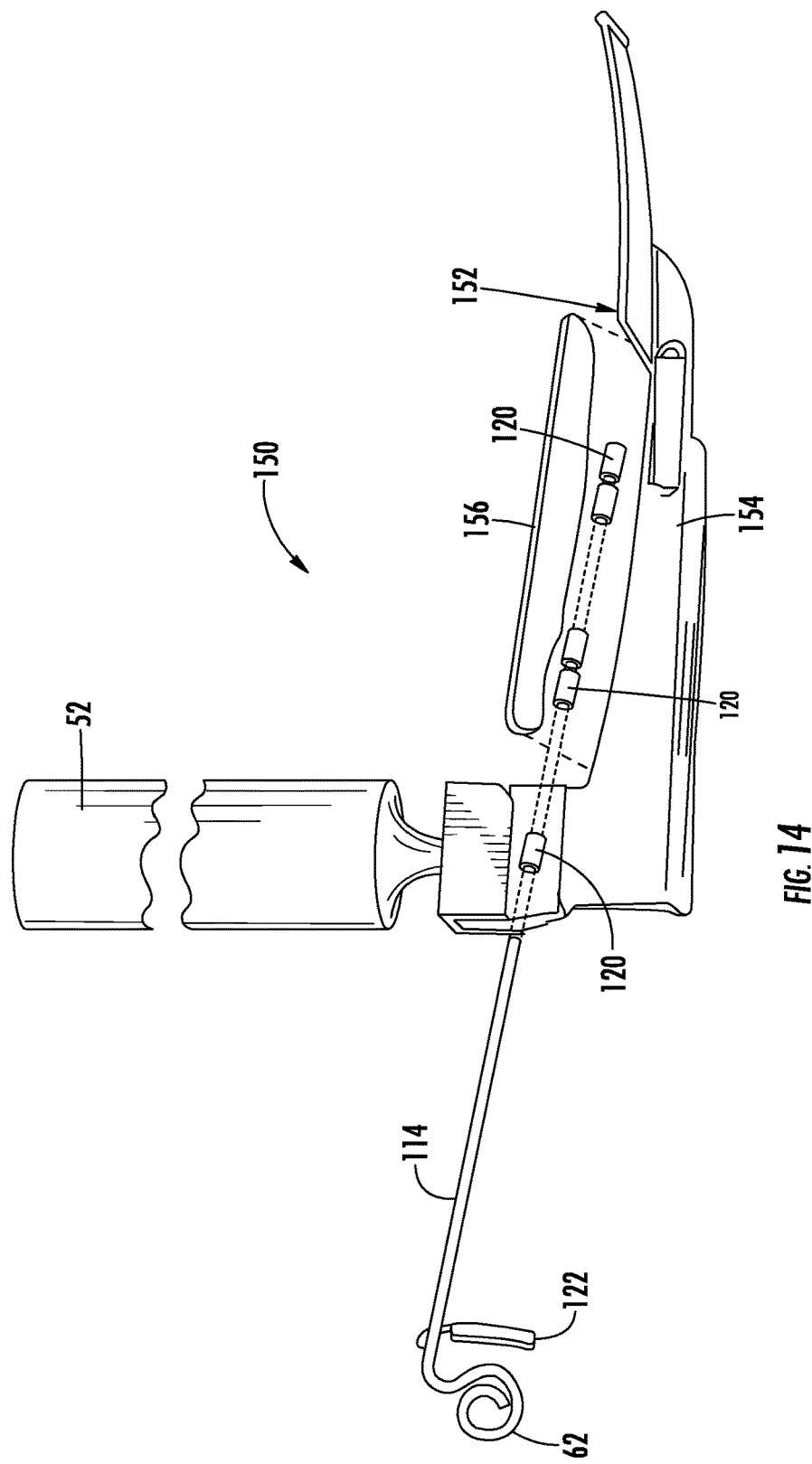
FIG. 14 is an exploded perspective view of the laryngoscope as shown in FIG. 13.
Figure 15:
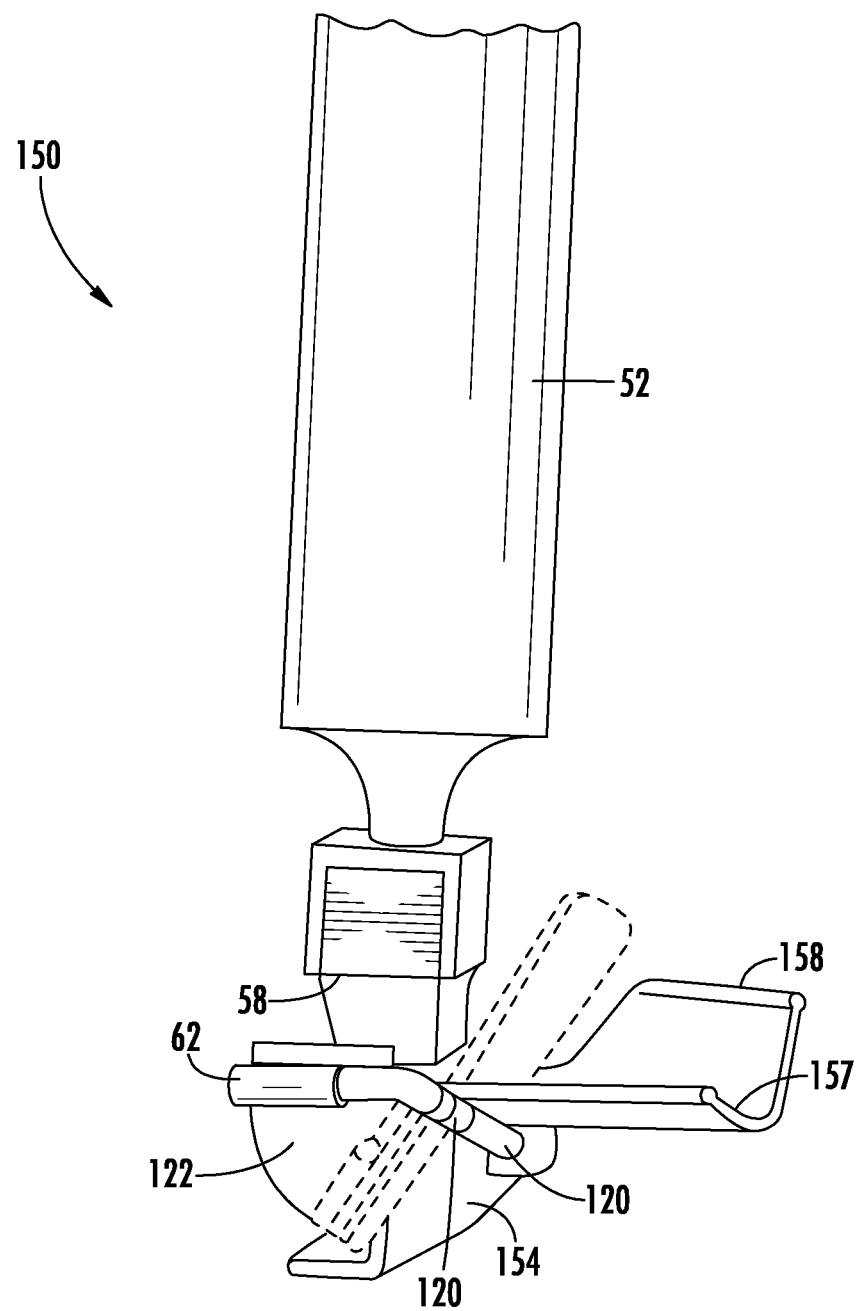
FIG. 15 is a rear elevation view of the laryngoscope as shown in FIG. 13 with the portion of the blade shown in the first position and the second position depicted in dashed lines.

FIG. 12 shows this embodiment of the laryngoscope 100 in use, with the tongue deflector 106 rotated relative to the stationary portion 104 of the blade 102 causing the tongue-contacting surface 107 of the tongue deflector 106 to move the tongue and associated tissue to expose the vocal cords and the larynx of a patient.

A third embodiment of a laryngoscope is shown in FIGS. 13-16 and generally designated at 150. The laryngoscope 150 comprises a blade 152, including a stationary portion 154 and a tongue deflector 156. In this embodiment, the stationary portion 154 of the blade 152 has an upper tongue-contacting surface 153 beginning at a distal end 158 and extending to a point intermediate along the length of the blade 152. The tongue deflector 156 is substantially rectangular and no wider than the blade 152 and is generally planar along its length. The tongue deflector 156 is positioned proximally of the tongue-contacting surface 153 of the stationary portion 154 of the blade 152 and extends substantially along the length of the proximal end 160 of the blade 152.

The tongue deflector 156 is rotatable about the longitudinal axis of the stationary portion 154 of the blade 152. In a first, home position of the tongue deflector 156, the edges of the tongue deflector 156 are abutted flush with the corresponding edges of the stationary portion 154 of the blade 152. The tongue deflector 156 is configured so that a tongue-contacting surface 157 of the tongue deflector 156 is substantially flush with the upper tongue contacting surface 153 of the stationary portion 154 of the blade 152. The surface of the tongue deflector 156 is shaped so as to provide surface continuity with the blade 152 when the tongue deflector 156 is in the home position. In this arrangement, the tongue deflector 156 provides no greater bulk that might obstruct either the visual field or working access distal to the tongue deflector 156 during an intubation procedure.

Figure 16:
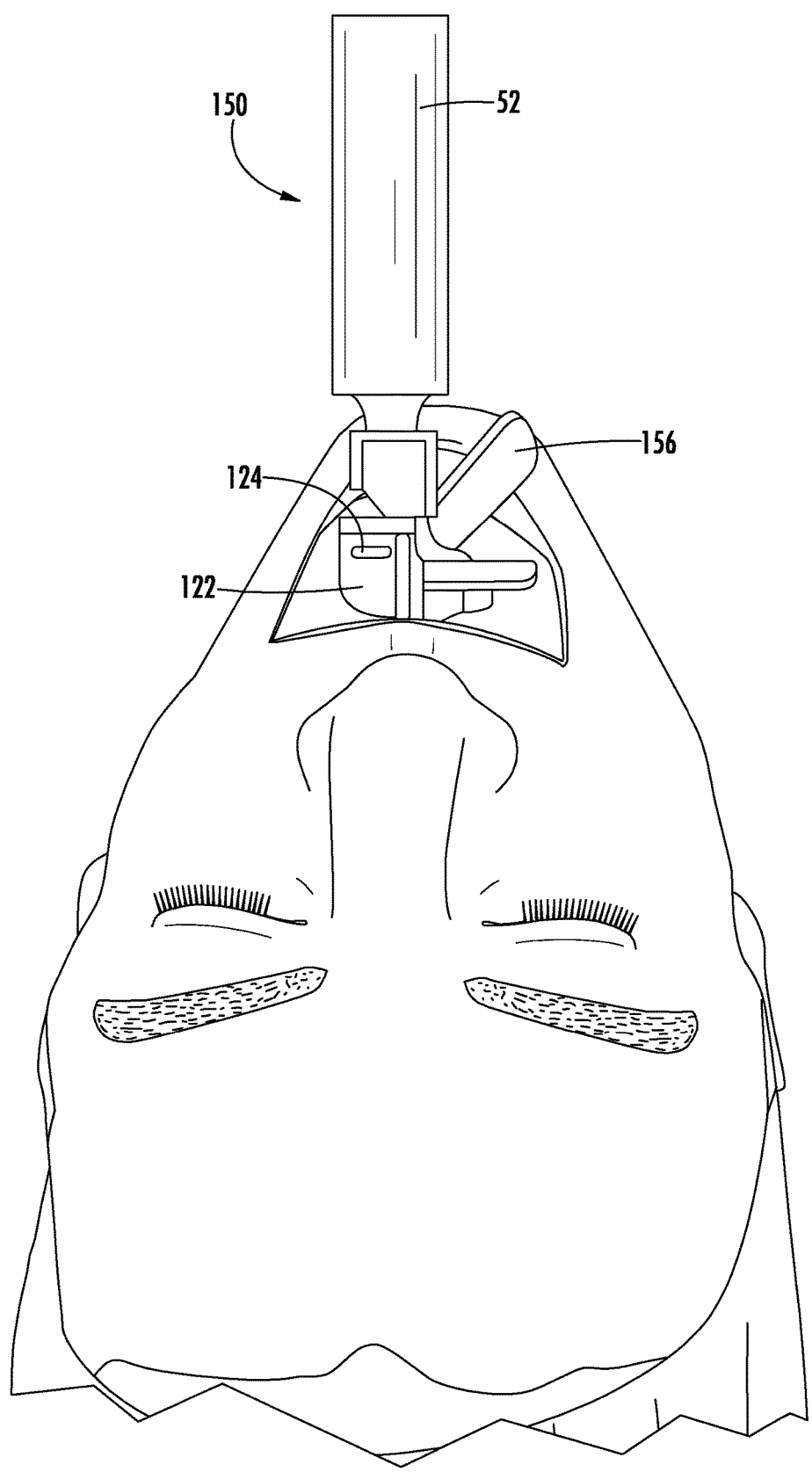
FIG. 16 is schematic elevation view of the laryngoscope as shown in FIG. 13 in position for use in a mouth of a patient with a portion of the face of the patient removed for clarity.

FIG. 16 shows the third embodiment of the laryngoscope 150 in use, rotating the tongue deflector 156 relative to the stationary portion 154 of the blade 152 causing the tongue-contacting surface 157 of the tongue deflector 156 to move the tongue and associated tissue to expose the vocal cords and the larynx of a patient.

Figure 17:
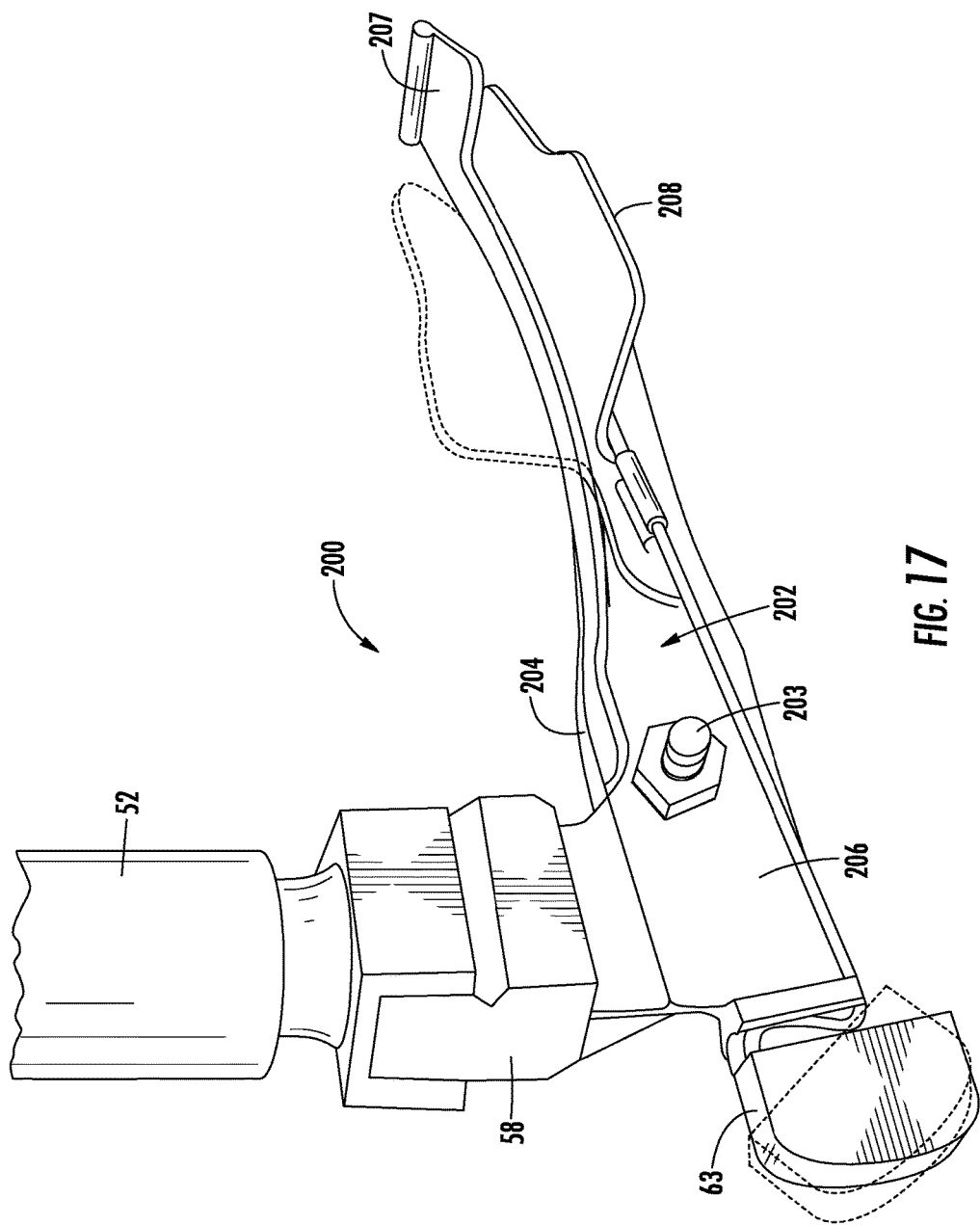
FIG. 17 is a rear left perspective view of still another embodiment of a laryngoscope with a portion of a blade shown in a first position and a second position depicted in dashed lines.
Figure 18:
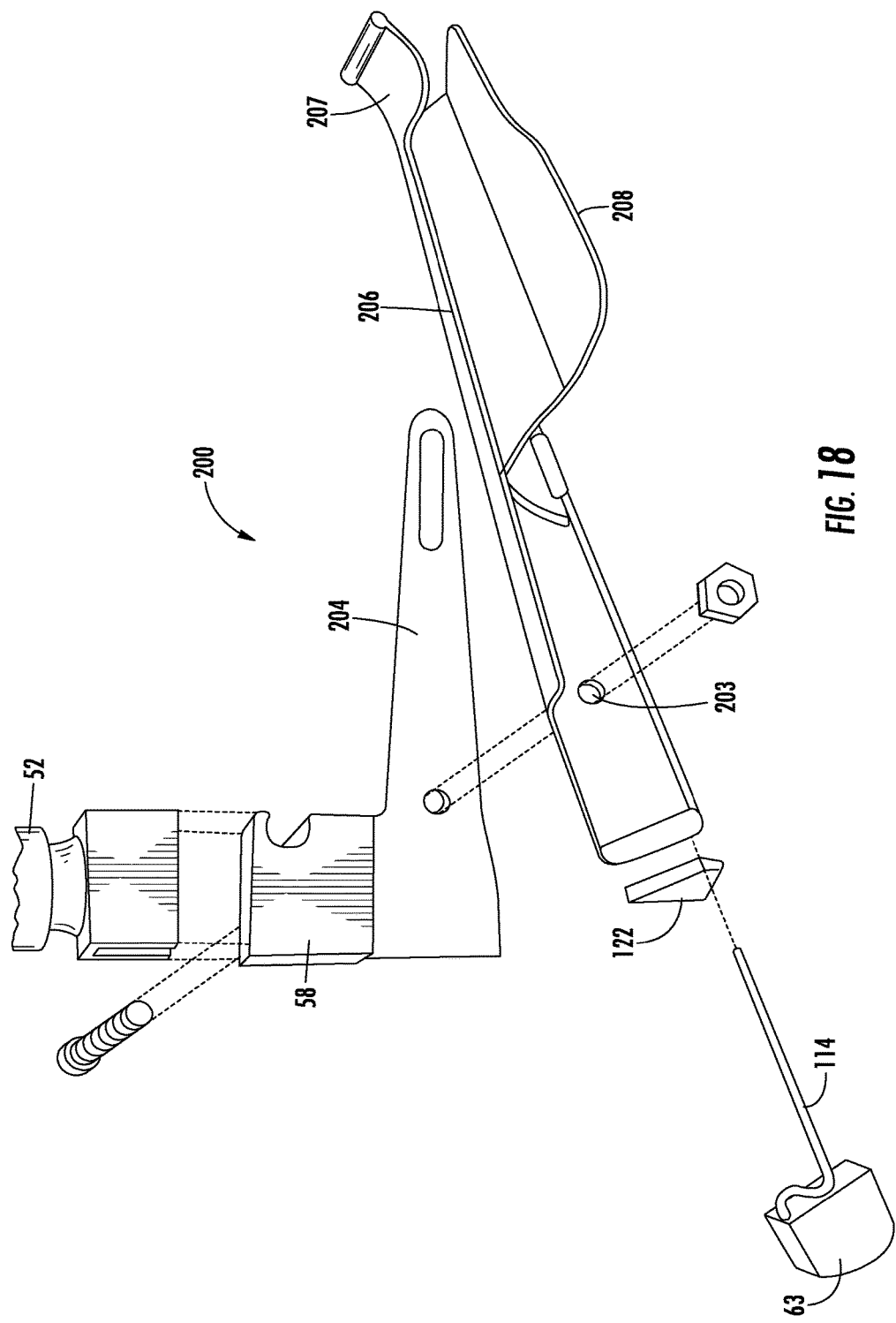
FIG. 18 is an exploded perspective view of the laryngoscope as shown in FIG. 17.
Figure 19:
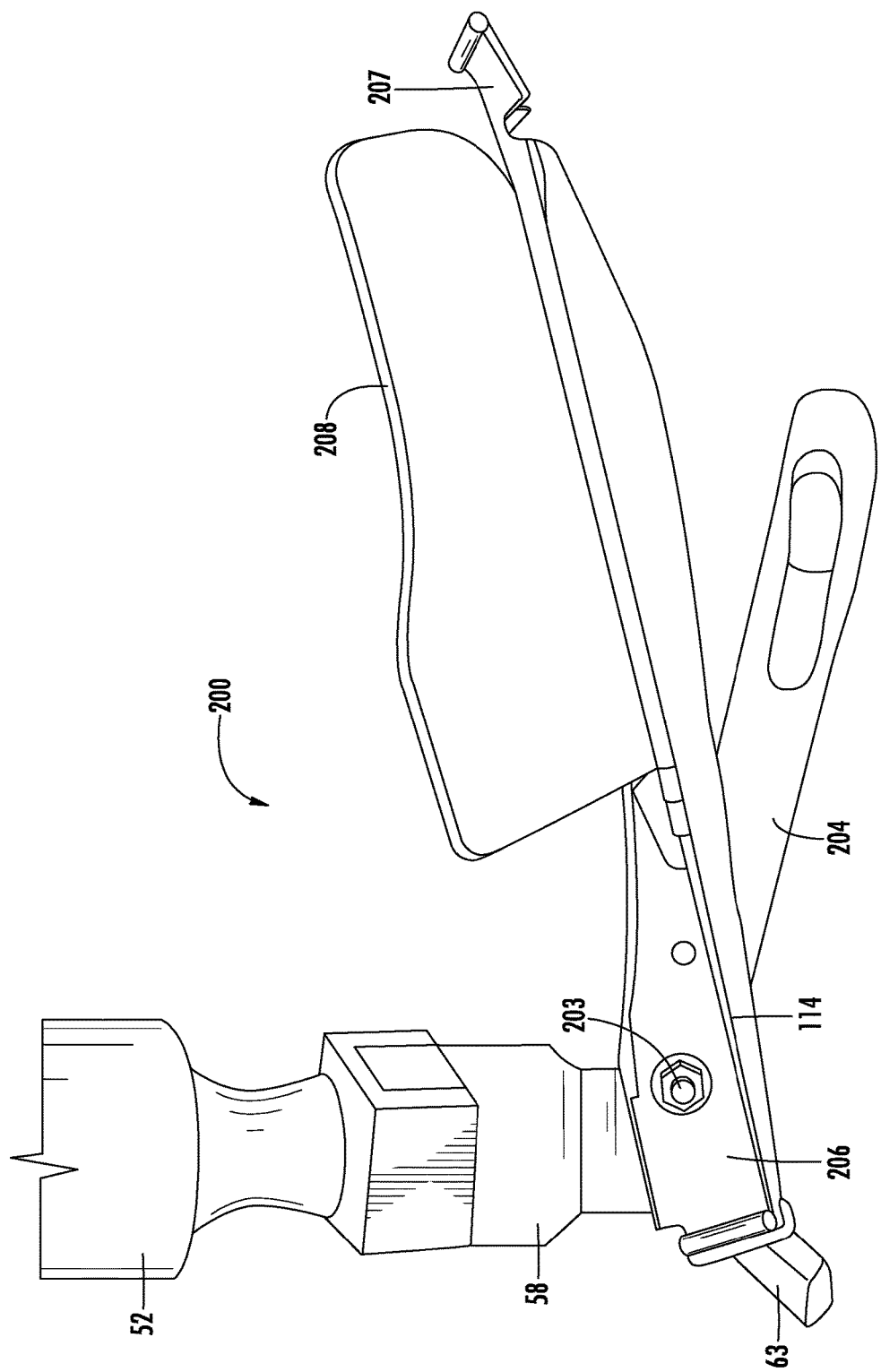
FIG. 19 is a right side elevation view of the laryngoscope as shown in FIG. 17 with the portion of the blade shown in the second position and the blade in a second position.
Figure 20:
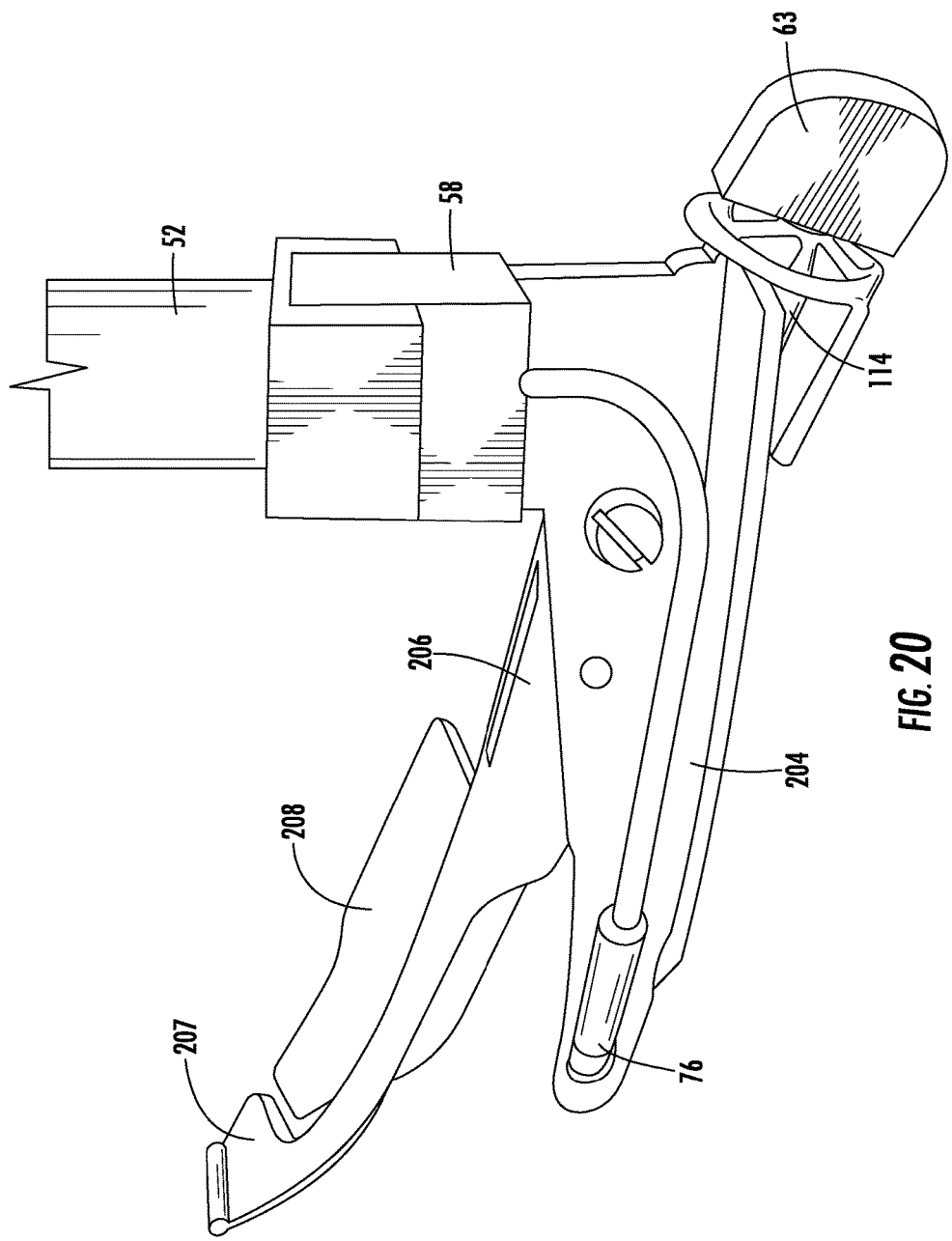
FIG. 20 is a left rear perspective view of the laryngoscope as shown in FIG. 17 with the blade in a second position.
Figure 21:
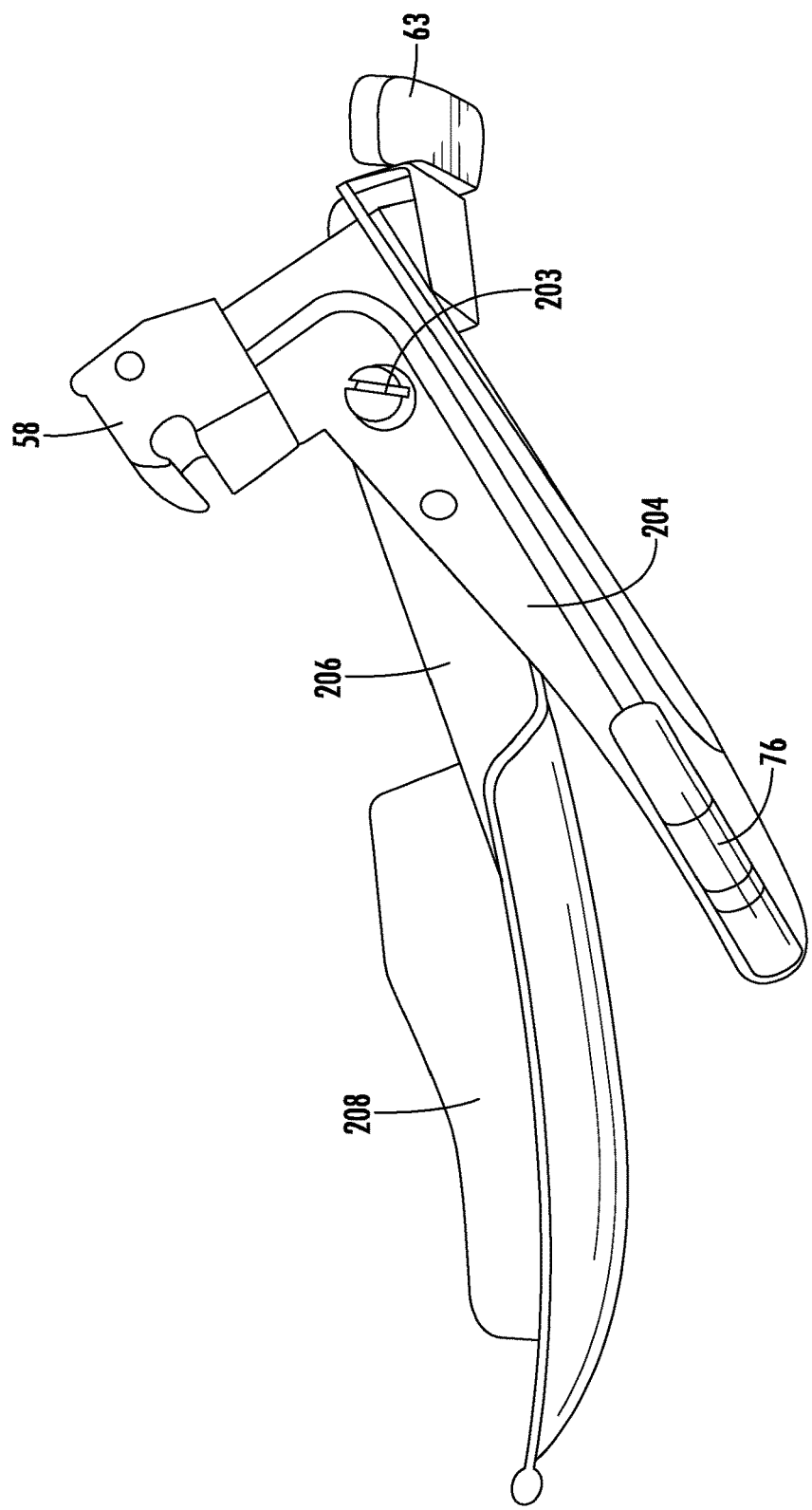
FIG. 21 is a left side elevation view of the laryngoscope as shown in FIG. 17 with the portion of the blade shown in the second position and the blade in the second position.
Figure 22:
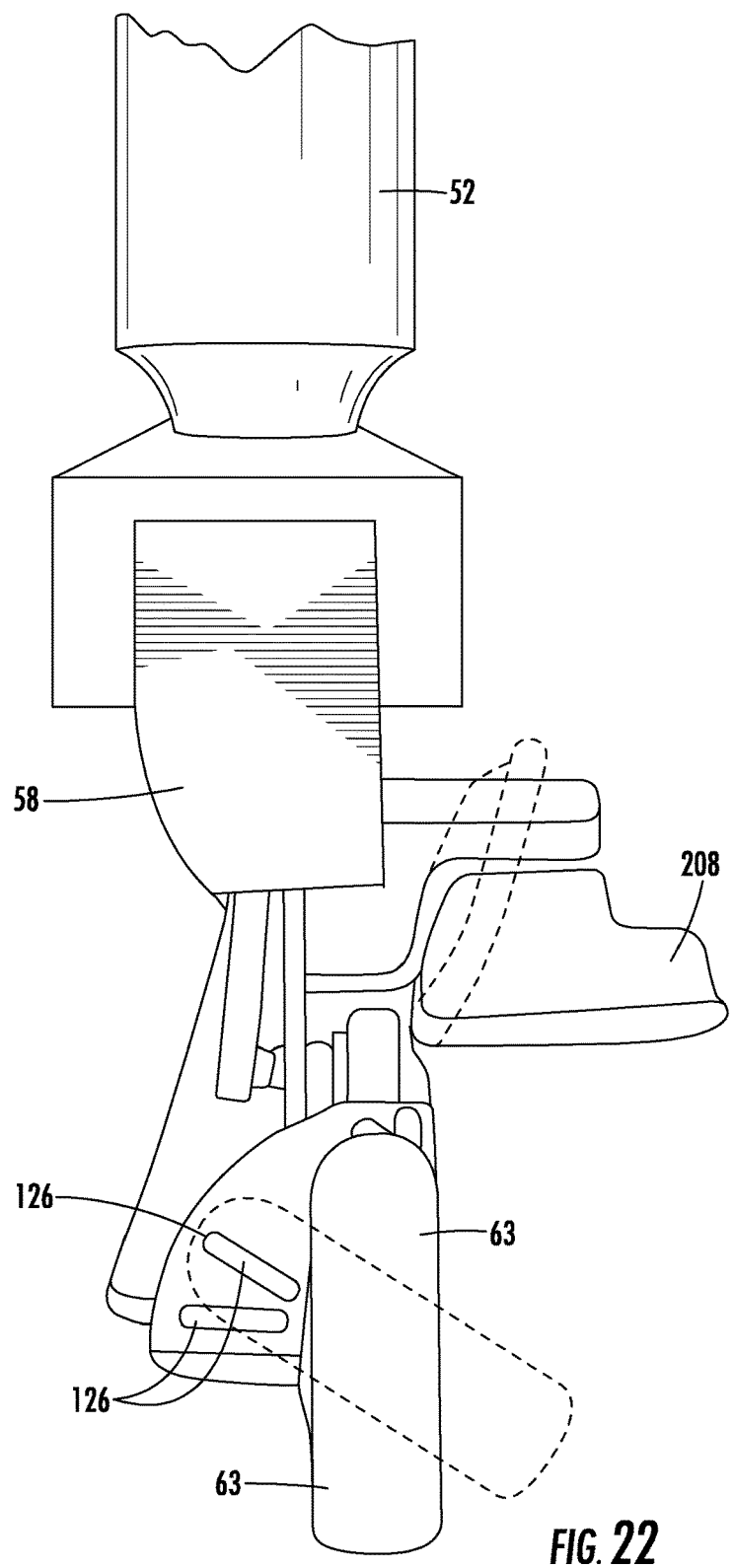
FIG. 22 is a rear elevation view of the laryngoscope as shown in FIG. 17 with the portion of the blade shown in the first position and the second position depicted in dashed lines and the blade in the second position.

A fourth embodiment of a laryngoscope is shown in FIGS. 17 and 18 and generally designated at 200. The laryngoscope 200 comprises a blade 202, including a stationary portion 204 and a pivoting portion 206 joined at a pivot point 203. The pivoting portion 206 of the blade 202 comprises a rotating tongue deflector 208. In this embodiment of the laryngoscope 200, the pivoting portion 206 of the blade 202 has an upper tongue-contacting surface 207 beginning at a distal end of the blade 202 and extending to a point intermediate along its length. The tongue deflector 208 is positioned proximally of the tongue-contacting surface 207 of the pivoting portion 206 of the blade 202. The tongue deflector 208 is configured to be rotatably mounted to the pivoting portion 206 of the blade 202 such that the tongue deflector 208 extends substantially along the length of the blade 202. In a first, home position of the tongue deflector 208, the edges of the tongue deflector 208 are abutted flush with the corresponding edges of the pivoting portion 206 of the blade. The tongue deflector 208 can rotate relative to pivoting portion 206 of the blade 202 to accomplish the tongue deflecting movement described herein for the other embodiments of the laryngoscope.

In use, the blade 202 is inserted into the mouth of the patient until the distal end of the blade 202 is positioned at the junction between the base of the tongue and the base of the epiglottis. With one hand holding the handle 52 of the laryngoscope 200, the user pivots the pivoting portion 206 of the blade 202 using the thumb or fingers of the other hand on on a finger grip 63 secured over the free end of the rod 114. Using the finger grip 63, the distal end of the pivoting portion 206 of the blade 202 is pivoted towards the handle 52 about the pivot point 203, and the tongue contacting surface 207 engages the tongue for elevating the tongue and exposing the larynx. The user may then rotate the finger grip 63 and connected rod 114 for pivoting the tongue deflector 208 using the thumb or fingers of the same hand. When the finger grip 63 is rotated relative to the blade 202, the rod 86 and connected tongue deflector 208 are rotated about their rotation axis causing the tongue-contacting surface of the tongue deflector 208 to sweep the tongue and associated tissue to further expose the vocal cords and the larynx of a patient.

Any one of the embodiments of the blade including the tongue deflector may be supplied as a sterile packaged, disposable item for single use. In an alternate embodiment, the blade would be constructed for repeated use and to resist degradation from repeated gas, chemical, or steam autoclave sterilization exposures. It is understood that the laryngoscope as described herein may comprise a range of handle or blade sizes and be suitable for use with adults, children or neonates, as well as being suitable for use in veterinary practice.

The embodiments of the laryngoscope described and shown herein have many advantages, including requiring less force for positioning and movement of the blade as compared to a conventional laryngoscope. Facilitating this sweeping of the tongue is achieved by applying a rotary force to the tongue deflector for moving the comparatively tongue muscle mass. The tongue deflector allows a user to engage the tongue in a manner that is not possible using conventional laryngoscopes. In addition, the locking function of the laryngoscope maintains continued airway patency once established.

As described above, the new blade can be used with conventional laryngoscope handles, which provide both ergonomic and power supply functions. Moreover, the tongue deflector can be made compatible for use on any type of laryngoscope blade known in the art, video scope blades, including Macintosh (curved) and Miller (straight) type blades which may be modified for the purposes and function as described herein. The laryngoscope is suitable for use by physicians, especially by anesthetists in procedures requiring the tracheal intubation of patients. The laryngoscope may also be used in veterinary practice. The tongue deflector may also be used with instruments other than a laryngoscope, such as an oral pharyngeal airway.

Although the laryngoscope has been shown and described herein in considerable detail with respect to only a few exemplary embodiments thereof, it should be understood by those skilled in the art that I do not intend to limit the laryngoscope to the embodiments since various modifications, omissions and additions may be made to the disclosed embodiments without materially departing from the novel teachings and advantages of the laryngoscope, particularly in light of the foregoing teachings. Accordingly, I intend to cover all such modifications, omission, additions and equivalents as may be included within the spirit and scope of the laryngoscope as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

I claim:

1. A laryngoscope for inserting into a mouth of a patient having a tongue, the laryngoscope comprising:
 a handle having a proximal end, a distal end and a longitudinal axis extending between the proximal end and the distal end of the handle;
 an elongate blade extending from the distal end of the handle in a plane angularly disposed with respect to the longitudinal axis of the handle, the blade including:
  a stationary portion having an upper surface, a proximal end, a distal end and a longitudinal axis extending between the proximal end and the distal end of the stationary portion, the proximal end of the stationary portion fixed to the distal end of the handle, and
  a movable portion having an upper surface for engaging the tongue of the patient, the movable portion mounted to the stationary portion of the blade for rotation about an axis substantially parallel to the longitudinal axis of the stationary portion of the blade; and
 an operating member manipulated by a user for rotating the movable portion of the blade from a first position to a second, rotated position relative to the stationary portion of the blade such that the upper tongue engaging surface of the movable portion of the blade moves toward the upper surface of the stationary portion,
wherein laryngoscopy of the patient by manipulation of the handle includes at least a rotating motion of the movable portion of the blade.

2. The laryngoscope as recited in claim 1, a locking mechanism for holding the operating member in a fixed angular position relative to the blade.

3. The laryngoscope as recited in claim 1, wherein the operating member comprises an elongate rod integrally formed with the movable portion of the blade.

4. The laryngoscope as recited in claim 1, further comprising means for directing light toward the distal end of the stationary portion.

* * * * *